United States Patent

Koblish et al.

[11] Patent Number: 5,855,581
[45] Date of Patent: *Jan. 5, 1999

[54] AWLS

[75] Inventors: Antony Koblish, Montclair, N.J.; Roger N. Levy, Pound Ridge, N.Y.

[73] Assignee: Howmedica Inc., New York, N.Y.

[ * ] Notice: The term of this patent shall not extend beyond the expiration date of Pat. No. 5,562,673.

[21] Appl. No.: 642,003

[22] Filed: May 2, 1996

Related U.S. Application Data

[62] Division of Ser. No. 205,679, Mar. 3, 1994, Pat. No. 5,562,673.

[51] Int. Cl.$^6$ .................................................. A61B 17/56
[52] U.S. Cl. ............................................. 606/80; 606/102
[58] Field of Search ................................. 606/80, 84, 85, 606/79, 89, 95, 93, 102, 167, 180; 29/78, 79, 80; 408/227, 228, 229, 230, 231; 128/774; 33/512, 511, 679.1, 544.4, 544.5, 555.3

[56] References Cited

U.S. PATENT DOCUMENTS

| | | | |
|---|---|---|---|
| 4,507,028 | 3/1985 | Matsushita | 408/230 |
| 4,751,922 | 6/1988 | DiPietropolo | 606/80 |
| 5,006,121 | 4/1991 | Hafeli | 606/85 |
| 5,108,405 | 4/1992 | Mikhail et al. | 606/96 |
| 5,190,548 | 3/1993 | Davis | 606/80 |
| 5,527,316 | 6/1996 | Stone et al. | 606/80 |
| 5,562,673 | 10/1996 | Koblish et al. | 606/80 |
| 5,573,537 | 11/1996 | Rogozinski | 606/80 |

*Primary Examiner*—Guy V. Tucker
*Attorney, Agent, or Firm*—Peter C. Richardson; Lawrence C. Akers; Elizabeth O. Slade

[57] ABSTRACT

An awl suitable for both opening up a bone canal and for sizing that bone canal so as to obviate the use of a Charnley awl and the use of 4 to 5 distal reamers comprises (a) a tapered distal cutting head having a pointed first end, and a second end; and (b) a shaft attached to the second end, such that the shaft has a multiplicity of grooves calibrated so as to indicate the diameter of the isthmus of the bone canal. Also provided is a method of opening up a bone canal and of measuring the diameter of the isthmus of the bone canal with a single instrument.

9 Claims, 3 Drawing Sheets

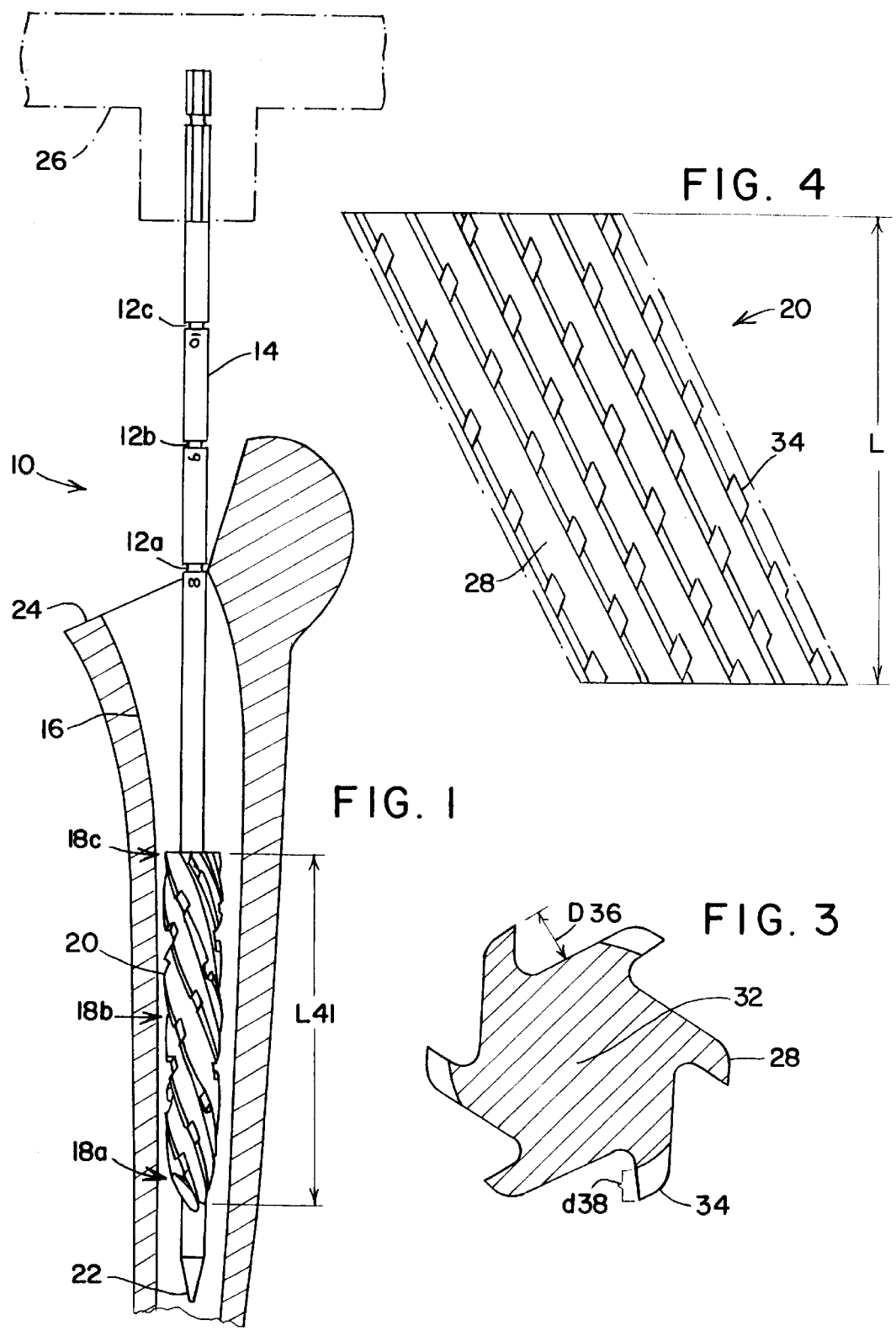

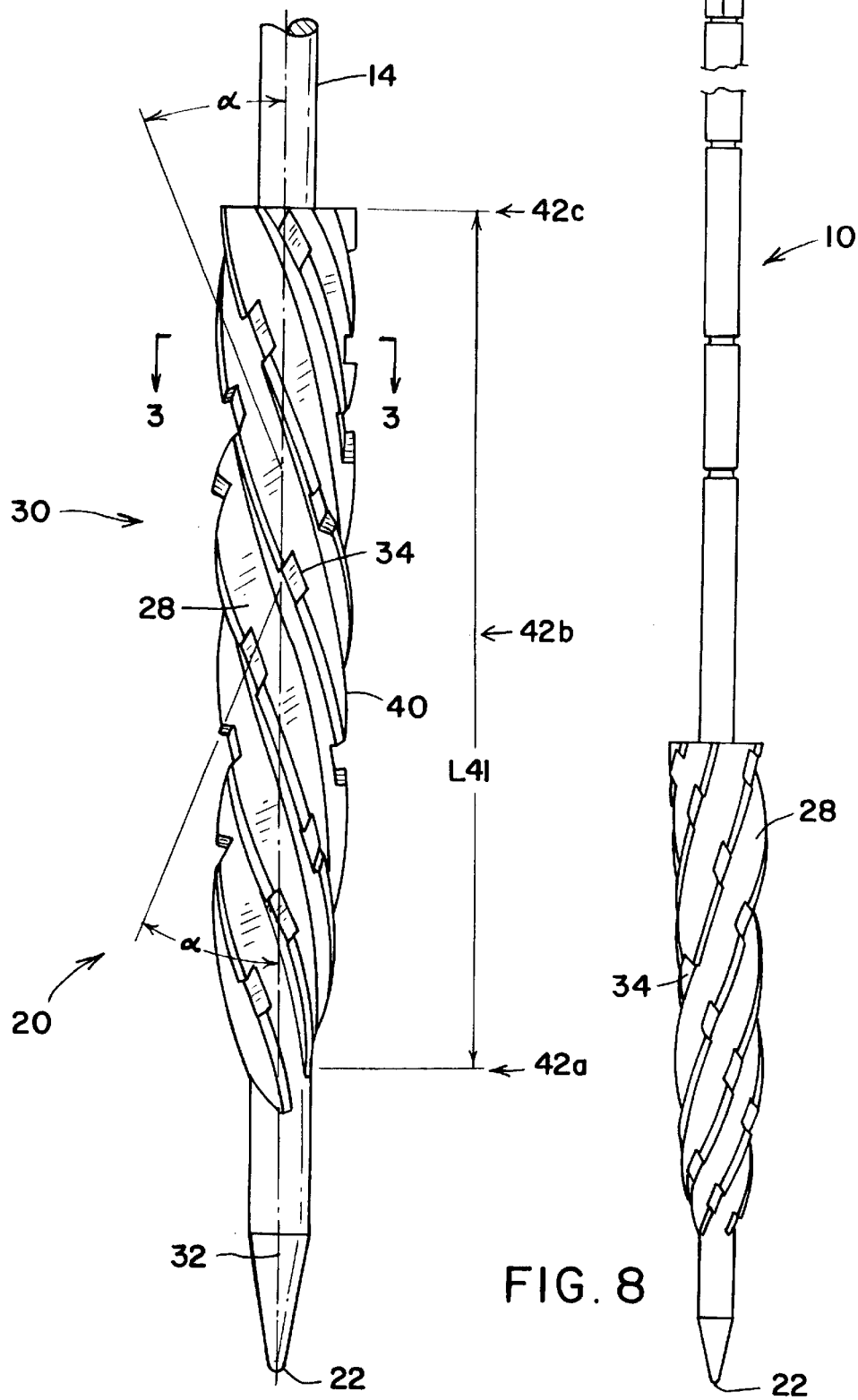

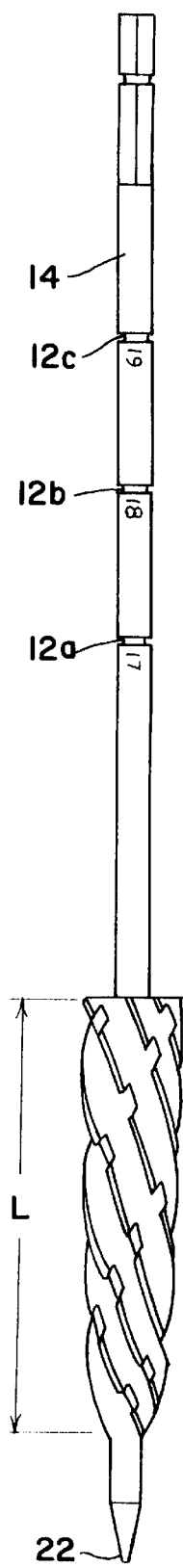
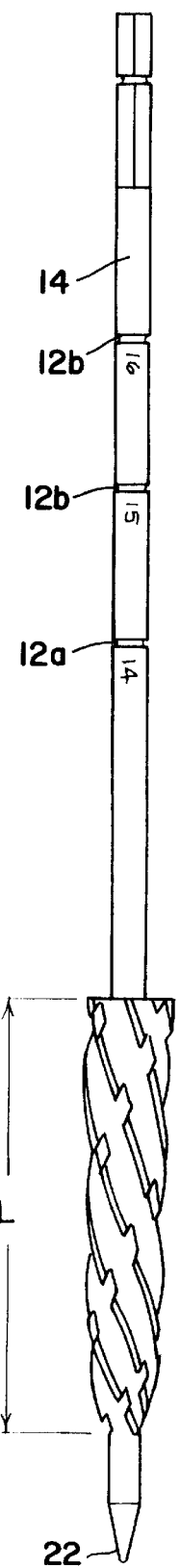
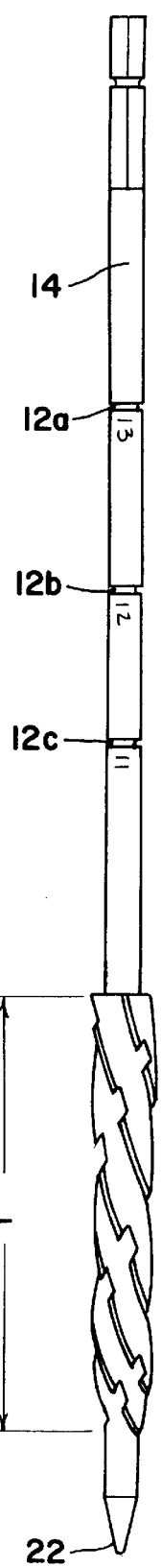

AWLS

This is a division of application Ser. No. 08/205,679, filed on Mar. 3, 1994, now U.S. Pat. No. 5,562,673.

FIELD OF THE INVENTION

This invention relates in general to awls and relates in particular to awls with special features and advantages for use in orthopedic surgery.

BACKGROUND OF THE INVENTION

Surgeons strive for accurate, replicable surgical techniques so that precise fits can be obtained between prothesis and bone. Increased contact area between bone and prosthesis has been shown to improve long-term fixation in cementless applications. Accurate bone preparation for cemented protheses will also provide improved fixation due to precise and optimal cement mantle thickness between bone and prosthesis. To accomplish "optimal" femoral envelope preparation, surgeons make use of instruments in a predetermined technique.

In the prior art, in performing total hip arthroplasty, preparation of the femoral envelope is traditionally divided into four steps, in general. In the first step, a starter awl (which is sometimes referred to as a "Charnley awl") is used to open the femur. In that step, a starter awl is used to define an opening in the proximal canal. Such starter awls are generally small diameter, straight-fluted reamers, which are manually introduced into the femoral canal to open a track into which subsequent progressive distal reamers may be introduced.

In the second step of the preparation of the femoral envelope, a short guide wire is passed into the femoral canal; and a set of four to five either rigid or flexible distal reamers with progressively larger sizes are passed into the canal until "circumferential cortical resonance" (which is also called "resistance to distal passage") is noted. The reamers should pass to the depth of the isthmus in the femoral canal (which is defined here as a constriction between the two larger parts of the femoral canal; that is, the isthmus is the narrow part of the femoral canal between the condyles and the proximal femur). In this second step, multiple iterations of distal reamers must be passed into the isthmus to size the passage up to the proper diameter.

In the third step of the traditional method in the prior art, the proximal portion of the femoral canal to the point of the isthmus is conically reamed. That is, the metaphyseal and diaphyseal regions are prepared using a multiplicity of proximal tapered midshaft reamers. These reamers have a non-cutting bullet tip that rides in the prepared isthmus distally. The tapered midshaft reamers remove proximal lateral bone and make the fourth step in the 4-step procedure easier.

The fourth step is to broach the metaphysis and diaphysis multiple times.

Thus, to summarize, the preparation sequence of the prior art is to use a starter awl, then distally ream the isthmus multiple times, then ream the proximal portion of the femoral canal (i.e., the metaphyseal and diaphyseal regions) multiple times, and then broach the metaphyseal and diaphyseal regions multiple times.

In the 4-step procedure, the last three steps must be completed multiple times, carefully using increasingly larger instruments in each iteration until final sizing to fit has been attained. These multiple iterations per step are time consuming, yet essential when performing hip surgery. Sizing up through multiple iterations minimizes the chances of damaging the femur by forcing too large an instrument into the bone.

It is an object of this invention to provide an apparatus and a kit of apparatuses for reducing the number of multiple iterations needed for preparation of the femoral canal.

A further object of this invention is to provide a method in which the number of iterations required in preparation of the femoral canal is significantly reduced.

Yet another object of this invention is a device and a kit of awls which can be used so as to both open the femoral canal and then size the distal portion of any human femoral canal using at most only two such awls and thereby obviating the use of the four to five distal reamers which in the past have been required generally in the second step of the 4-step procedure described above.

Yet another object of this invention is an awl which will be used both as a starter awl and will also size the femoral canal, with at most only two such awls being necessary for starting and sizing distally any human femoral canal, (i.e., performance of steps one and two described above, in which the femoral canal is opened and the isthmus is prepared).

SUMMARY OF THE INVENTION

According to the invention, an awl for use in orthopedic surgery for both opening up a bone canal and for sizing the distal portion of that bone canal (so as to obviate the use of the 5–6 instruments needed in the prior art in steps (1) and (2) described above), comprises: a tapered distal cutting head having a pointed first end and a second end; and (b) a shaft attached to the second end, wherein the shaft has grooves calibrated so as to indicate the diameter of the isthmus of the bone canal.

Also according to the invention, in a preferred embodiment, the grooves on the shaft of the awl indicate the diameter of the isthmus of the bone canal by correlating that diameter with the depth reached by the awl as measured at the calcar of the bone canal.

In another embodiment, according to the invention, a kit comprises four awls of selected sizes, each for use as both a starter awl and for preparation of the isthmus of any human bone canal, such that only two of the four awls in the kit need be used for performing steps 1 and 2 described above.

Also according to the invention, a method of opening up a bone canal and of measuring the diameter of the isthmus of that bone canal comprises: (a) inserting an awl according to the invention into the bone canal at the calcar of the bone canal until resistance to distal passage of the awl at the isthmus is noted; (b) noting the depth reached by the awl at the calcar of the bone canal when the resistance occurs; and (c) correlating the depth reached by the awl with the corresponding diameter of the isthmus of the bone canal.

Further according to the invention, a method of preparing and further cleaning the isthmus of the bone canal so that the isthmus is a smooth, cylindrical shape comprises the additional step (in addition to the three steps a, b, and c just described) of further cutting the bone canal with an awl of the invention which is of slightly larger size than that used in steps a, b, and c, so as to form the isthmus into a smooth, cylindrical shape.

It is believed that the awl of the invention which both opens up the femoral canal and provides information about the size of the isthmus of the bone canal has not previously been known; and in particular, it is believed that it especially has not been known to provide a kit of four such awls of increasingly larger sizes such that any human femoral bone canal can be prepared by a doctor skilled in this art area by using at most only two such awls. The reduced number of iterations necessary for preparation of the bone canal with the use of the awls of the invention is therefore very important for saving time in the operating room and for cost containment in the cost-saving healthcare environment of today.

It is noted that the multiple iterations described above for steps three and four will still need to be used with the awls of the invention, which minimize the number of surgical instruments required for opening up the bone canal (in step one, described above), and for preparation of the isthmus (in step two, described above).

DESCRIPTION OF THE PREFERRED EMBODIMENTS

BRIEF DESCRIPTION OF THE DRAWING

FIG. 1 is a plan view of an embodiment of an awl of the invention shown located within a femoral canal, showing the calcar region of the bone, the markings on the shaft of the awl indicating three diameters of the awl at 3 positions at its tapered distal cutting head.

FIG. 2 shows an enlarged tapered cutting head of the device as shown in FIG. 1.

FIG. 3 is a cross-sectional view taken along the line 3—3 in FIG. 2.

FIG. 4 is a developed view of an embodiment of the awl of the invention. In this figure, 6 main cutting flutes are shown, and 3 chip breakers are shown.

FIGS. 5, 6, and 7 show 3 embodiments of the awl of the invention, in FIG. 5, the markings on the shaft of the awl being 17-18-19, which numerals correspond to the diameter of the awl in mm. at three locations. Correspondingly, FIG. 6 shows an awl of smaller diameters, with the diameters being 14, 15, and 16 millimeters, corresponding to three diameters of the awl. In FIG. 7, an even smaller awl of the invention is shown, with markings on the shaft indicating 11, 12, and 13 millimeters (which indicate diameters of the awl at 3 different positions on the tapered distal cutting head.)

FIG. 8 shows an alternative embodiment of an awl according to the invention, which although not preferred, can (if desired) be used. This embodiment shows six main cutting flutes in a right handed helix and three chip breakers in a left handed helix.

DETAILS DESCRIPTION OF THE DRAWINGS

Referring to the drawing, in FIG. 1, an embodiment of an awl (10) according to the invention is shown located within a femoral canal (16). Markings on the shaft which are 8, 9, and 10 millimeters indicate diameters of the awl at different positions on the cutting head. The three shaft markings labeled 12a, 12b, 12c indicate the diameters 18a, 18b, and 18c, which are diameters of the awl 10 at 3 different locations on its tapered distal cutting head 20. The awl 10 is inserted into the femoral canal 16 until its pointed end 22 first opens the femoral canal 16 near the calcar 24. The awl 10 is manually inserted by means of a detachable handle 26, and the awl 10 is rotated slowly until resistance to distal passage of the awl is noted. At that point, the awl is approaching the isthmus (i.e., the narrowing of the intramedullary canal, which is located between the condyles and the calcar, (not shown in FIG. 1)).

Shown in FIG. 2 (and in FIGS. 1 and 3–7) an awl 10 having (in this preferred embodiment) six main flutes 28 is shown, with the main flutes 28 being formed in a left-handed helical configuration, which presents an aggressive helical tooth configuration. That is, the six main flutes shown in FIG. 2 form a left-handed helix 30. Awl 10 has a long axis 32. The main cutting flutes 28 are positioned at an angle a with respect to long axis 32. Angle $\alpha$ can be any angle within the range from slightly greater than 0° up to a relatively sharp angle of about 75°. However, preferably angle $\alpha$ will be within the range from about 20° to 35° and most preferably will be within the range from 27° to 29°, so as to form an aggressive helical tooth configuration of the main flutes. A left-handed helix of the main flutes is preferred for reasons of safety.

Also shown in FIG. 2 are three chip breakers 34 which are in an oppositely handed configuration (in this case right-handed helical configuration; and they will be positioned with respect to long axis 32 also at an angle $\alpha$. Also shown in FIG. 2 are shaft 14 and pointed end 22 of awl 10. The depth D 36 per side of main cutting flutes 28 is shown. Also as best shown in FIG. 3 is the depth d 38 of chip breakers 34, which in a preferred embodiment is one-half of the depth per side of main cutting flutes D 36 (also shown in FIG. 3). These depths are shown more clearly in FIG. 3 and in FIG. 4. Also shown in FIG. 2 (and in FIGS. 1, 5, 6, and 7) are tapered distal cutting heads 20 which in a most preferred embodiment are all tapered with a three millimeter taper 40 per length L (which in a preferred embodiment is 3 inches). Also shown in FIG. 2 are points 42a, 42b, 42c, which are points spaced equidistantly on the tapered distal cutting head 20 at which the diameter of the awl is measured.

In FIG. 3, taken along the line 3—3 in FIG. 2, the six main cutting flutes 28 are shown, as well as long axis 32 and three chip breakers 34.

In FIG. 4, a developed view of an embodiment of the awl of the invention is shown, which (for purposes of visualizing the components of the tapered distal cutting head 20) has been drawn so that it appears in an unrolled position. Corresponding parts of the tapered distal cutting head 20 are numbered correspondingly, as were described above for FIG. 2.

For FIGS. 5, 6, 7, and for FIG. 1, the four awls which can be used to form a kit such that any human femoral canal can be both opened up and sized by using at most only 2 of these four awls are shown. In these four awls, numerals are indicated on the shaft 14 of the awl 10 such that the marking groups correspond to the diameter of the tapered distal cutting head 20 at three points. Each of these four awls has a tapered distal cutting head 20 which has a 3 millimeter taper 40 per length L (which is 3 inches in this preferred embodiment).

In FIG. 8, although not generally preferred, an embodiment showing an awl 10 having the main cutting flutes 28 positioned in a right handed helix and the chip breakers positioned in a left handed helix is provided.

It is noted that the awl of the invention can be used for other uses in orthopedic surgery, provided that the calibrations on the shaft and the taper are suitably modified. That is, the invention is not limited to use in femoral canals.

We claim:

1. An awl for both opening up a bone canal and for measuring the size of the diameter of said bone canal so as to obviate use of a Charnley awl and use of 4 to 5 distal reamers, said awl comprising:

(a) a tapered distal cutting head having (1) a pointed first portion having a sharp, substantially needle-like shape for punching holes and (2) a second portion adjacent to said first portion, said second portion having a multiplicity of cutting surfaces and a tapered shape which tapers from a smallest diameter to a largest diameter; and (b) a shaft attached to said second portion wherein said shaft has a multiplicity of grooves calibrated so as to indicate at least said largest diameter and said smallest diameter and thereby to permit reading off the diameter of the isthmus of said bone canal.

2. An awl according to claim 1, wherein said grooves indicate the diameter of said isthmus by correlating one of several diameters of said awl with the depth reached by said awl as measured at the calcar of said bone canal.

3. An awl according to claim 2, wherein said awl has an aggressive helical tooth configuration comprising a multiplicity of main flute angles measured from the long axis of the awl lying within the range from about 20° to about 35°.

4. An awl according to claim 3, wherein each main flute angle lies within the range from about 27° to about 29° as measured from the long axis of said awl and wherein said second portion has a length of about 3 inches.

5. An awl according to claim 3, wherein said aggressive helical tooth configuration is a left-handed helical configuration of main flutes.

6. An awl according to claim 5 wherein said awl is self-tapping and has right handed chip breakers.

7. An awl according to claim 6 and including also a detachable handle attached to said shaft.

8. A kit comprising at least a first awl according to claim 1 and a second awl according to claim 1, wherein said first awl has a first tapered distal cutting head with a first largest diameter and wherein said second awl has a second tapered distal cutting head with a second largest diameter and wherein said first largest diameter is smaller than said second largest diameter.

9. A kit according to claim 8, wherein said shaft of each of four progressively larger diameter awls in said kit has one of a set of three markings located on said shaft comprising the sets of numerals 8-9-10, 11-12-13, 14-15-16, and 17-18-19, said numerals being measured in mm. and corresponding to the diameter of the tapered distal cutting head at three points.

* * * * *